(12) United States Patent
Ricci et al.

(10) Patent No.: US 10,705,038 B2
(45) Date of Patent: Jul. 7, 2020

(54) SYSTEMS AND METHODS FOR DETECTING CHIPS IN FLUID OF AIRCRAFT ENGINE

(71) Applicant: PRATT & WHITNEY CANADA CORP., Longueuil (CA)

(72) Inventors: Thomas Trevor Ricci, Kirkland (CA); Simon Sai-Ming Lam, Scarborough (CA); James Robert Jarvo, Saint-Bruno-de-Montarville (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 0 days.

(21) Appl. No.: 16/398,492

(22) Filed: Apr. 30, 2019

(65) Prior Publication Data

US 2019/0257777 A1 Aug. 22, 2019

Related U.S. Application Data

(63) Continuation of application No. 15/357,282, filed on Nov. 21, 2016, now Pat. No. 10,317,354.

(60) Provisional application No. 62/369,601, filed on Aug. 1, 2016.

(51) Int. Cl.
| | |
|---|---|
| *G01N 27/06* | (2006.01) |
| *G01N 33/22* | (2006.01) |
| *F16N 29/04* | (2006.01) |
| *G01N 27/04* | (2006.01) |
| *G01N 33/28* | (2006.01) |

(52) U.S. Cl.
CPC ............. *G01N 27/06* (2013.01); *F16N 29/04* (2013.01); *G01N 27/041* (2013.01); *G01N 33/22* (2013.01); *G01N 33/2858* (2013.01); *F16N 2250/32* (2013.01)

(58) Field of Classification Search
CPC ......... G01N 15/0656; G01N 2015/149; G01N 27/745; G01N 33/54326; G01N 15/147; G01N 2446/00; G01N 27/4148; G01N 29/022; G01N 29/34; G01N 35/085; G01N 15/1484; G01N 2015/0288; G01N 2015/1006; G01N 2035/00237; G01N 2035/00356; G01N 2035/1034; G01N 35/0098; G01N 27/06; G01N 27/041; G01N 33/2858; G01N 33/22; G01R 33/1269; G01R 33/093; G01R 33/096; G01R 33/12; F16N 2250/32; F16N 29/04
See application file for complete search history.

(56) References Cited

U.S. PATENT DOCUMENTS

| | | |
|---|---|---|
| 2,878,342 A | 3/1959 | Arthur |
| 4,100,491 A | 7/1978 | Newman et al. |
| 4,323,843 A | 4/1982 | Batham |

(Continued)

*Primary Examiner* — Vinh P Nguyen
(74) *Attorney, Agent, or Firm* — Norton Rose Fulbright Canada LLP

(57) ABSTRACT

There is described herein methods and systems for detecting of metallic chips in a fluid system of an aircraft engine. A resistance value is measured across a magnetic chip detector mounted to a fluid system of the aircraft engine. The resistance value is transmitted to an engine computer of the aircraft engine. In the engine computer, The resistance value is compared to a first threshold and a first warning indicative of a chip in the fluid is issued when the resistance value exceeds the first threshold.

19 Claims, 7 Drawing Sheets

(56) References Cited

U.S. PATENT DOCUMENTS

| | | | |
|---|---|---|---|
| 4,731,578 A * | 3/1988 | Tsaprazis | F16N 29/00 |
| | | | 324/204 |
| 5,782,141 A | 7/1998 | Schoolcraft | |
| 6,445,177 B1 | 9/2002 | Higgins | |
| 7,106,075 B2 | 9/2006 | Hu | |
| 7,886,875 B2 | 2/2011 | Shevchencko et al. | |
| 8,018,237 B2 * | 9/2011 | Takahashi | G01N 33/2858 |
| | | | 324/204 |
| 8,184,290 B2 | 5/2012 | Hertens et al. | |
| 9,316,630 B2 | 4/2016 | Hodgkinson et al. | |
| 10,180,075 B1 * | 1/2019 | Andrus | F01D 17/02 |
| 10,254,210 B2 | 4/2019 | Weiser | |
| 2014/0347032 A1 | 11/2014 | Reed et al. | |

* cited by examiner

SYSTEMS AND METHODS FOR DETECTING CHIPS IN FLUID OF AIRCRAFT ENGINE

CROSS-REFERENCE TO RELATED APPLICATIONS

The present application is a continuation of U.S. patent application Ser. No. 15/357,282 filed on Nov. 21, 2016, now U.S. Pat. No. 10,317,354, which claims the benefit of U.S. Provisional Patent Application No. 62/369,601 filed on Aug. 1, 2016, the contents of which are hereby incorporated by reference.

TECHNICAL FIELD

The disclosure relates generally to aircraft engine operation and, more particularly, to the detection of chips in fluid of the aircraft engine.

BACKGROUND OF THE ART

Magnetic chip detectors are generally mounted to a fluid system of an aircraft engine to assess the presence or absence of metallic chips in the fluid. The metallic chips may result from normal engine wear and tear and/or major engine failures, which causes metal chips to break loose from engine parts and circulate in the engine fluid.

Some magnetic chip detectors have two spaced-apart magnetic prongs positioned in the fluid such that, when attracted metallic chips bridge the gap between the two prongs, an electronic circuit of the magnetic chip detector is closed which may cause an indication in the cockpit of the aircraft to be activated. Other magnetic chip detectors have only one magnet and the gap to be bridged is between the magnet and a housing.

As the presence of metal chips in engine fluid is indicative of engine condition, there exists a need to improve on chip detection for aircraft engines.

SUMMARY

In accordance with one aspect, there is provided a method for detecting chips in fluid of an aircraft engine. The method comprises dynamically setting a first threshold in an engine computer for detecting chips in the fluid; measuring a resistance value across a first magnetic chip detector mounted to a fluid system of the aircraft engine and transmitting the resistance value to the engine computer of the aircraft engine; comparing, in the engine computer, the resistance value to the first threshold; and issuing, from the engine computer, a first warning indicative of a chip in the fluid when the resistance value exceeds the first threshold.

In accordance with another aspect, there is provided a chip detection system for an aircraft engine. The detection system comprises a magnetic chip detector mounted to a fluid system of the aircraft engine, a resistance measurement circuit connected with the magnetic chip detector and configured for measuring a resistance value across the magnetic chip detector, and an engine computer coupled to the resistance measurement circuit. The engine computer is configured for dynamically setting a first threshold in the engine computer for detecting chips in the fluid, receiving the resistance value from the resistance measurement circuit, comparing the resistance value to the first threshold, and issuing a first warning indicative of a chip in the fluid when the resistance value exceeds the first threshold.

In accordance with yet another aspect, there is provided a method for detecting chips in fluid of an aircraft engine. The method comprises measuring a resistance value across a magnetic chip detector mounted to a fluid system of the aircraft engine and transmitting the resistance value to an engine computer of the aircraft engine. The method further comprises, in the engine computer, comparing the resistance value to a first threshold and issuing a first warning indicative of a chip in the fluid when the resistance value exceeds the first threshold.

In accordance with another aspect, there is provided a method for detecting chips in fluid of an aircraft engine. The method comprises measuring a resistance value across a first magnetic chip detector mounted to a fluid system of the engine and transmitting the resistance value to an engine computer of the aircraft engine. The method further comprises, in the engine computer, converting the resistance value to a chip size and sending the chip size to an aircraft display. The method also comprises displaying the chip size on the aircraft display.

DESCRIPTION OF THE DRAWINGS

Reference is now made to the accompanying figures in which.

DETAILED DESCRIPTION

Knowledge of the size of the metal chips that are present in the fluid is used to manage operation of an aircraft engine. Large metal chips can indicate a major engine failure and can require immediate aircraft operator action (e.g., shut-down engine during flight), while small metal chips (often called "fuzz") are typically caused by normal engine wear and tear, and action can be delayed to the next maintenance interval.

There is described herein methods and systems for detecting of metallic chips in a fluid system of an aircraft engine. The chip is detected based on the measurement of a resistance value across a magnetic chip detector mounted to the fluid system. An engine computer of the aircraft engine is configured to compare the resistance value to a threshold and to issue a warning if the resistance value exceeds the threshold or a fault is detected in the system.

Figure 1:
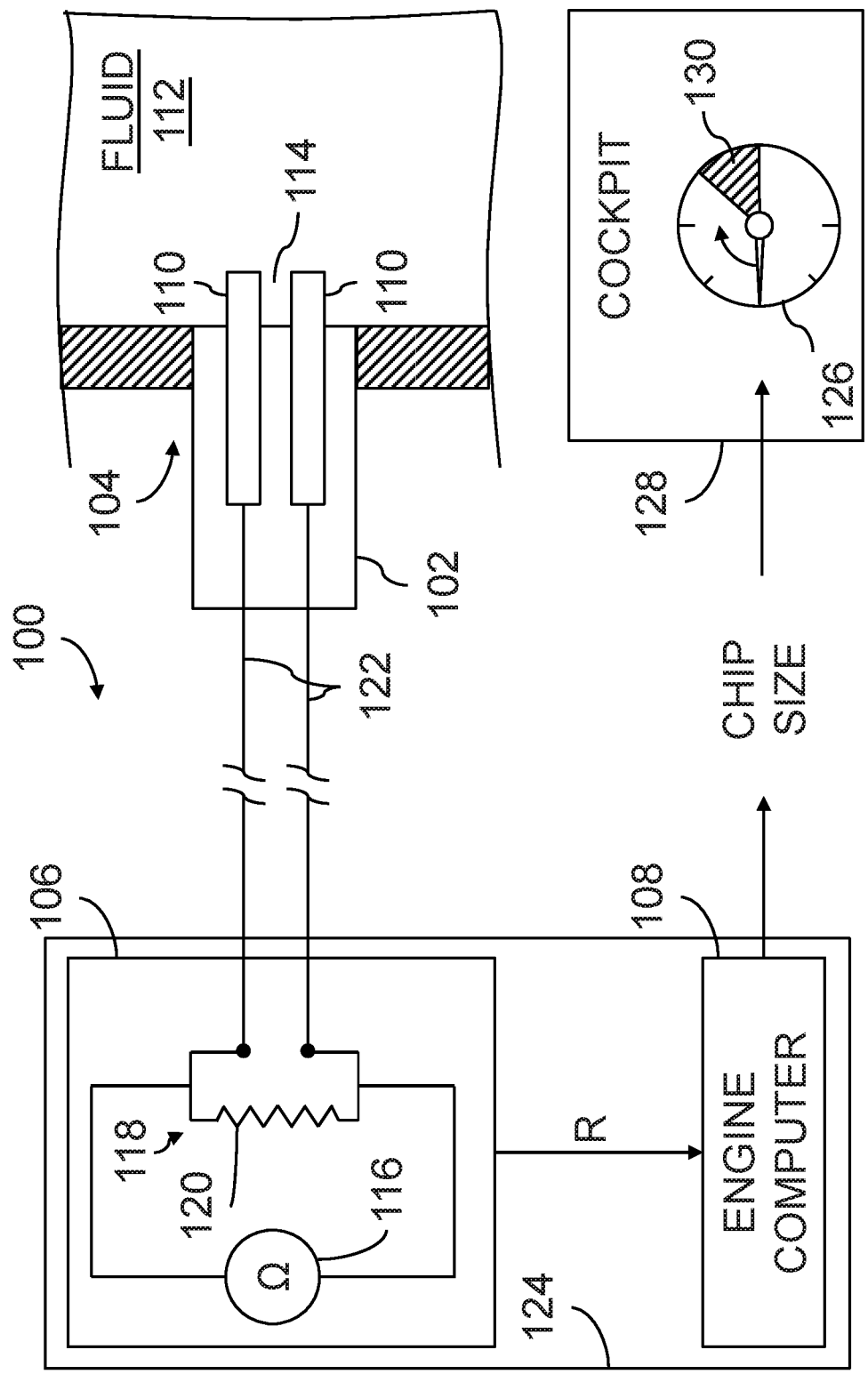
FIG. 1 is a schematic view of an example of a chip detection system for an aircraft engine.

With reference to FIG. 1, there is illustrated a chip detection system 100 for an engine of an aircraft. The aircraft may be any type of aircraft with an engine, such as a fixed-wing aircraft, a rotary-wing aircraft, and a jet aircraft. The engine may be any type of internal combustion engine, such as gas turbine engines, jet engines, and the like.

For example, the engine may be a turbofan engine, a turboprop engine, or a turboshaft engine. Other engines may also apply.

As depicted, the detection system 100 includes a magnetic chip detector 102 mounted to a fluid system 104 of the aircraft engine, a resistance measurement circuit 106 and an engine computer 108.

The engine computer 108 may be provided in the form of any engine controlling devices such as an engine control unit (ECU), an engine electronic controller (EEC), an engine electronic control system, and a Full Authority Digital Engine Controller (FADEC). As described herein, the detection system 100 may be used for health monitoring and fault detection.

In this example, the magnetic chip detector 102 has two magnetic prongs 110 positioned in the fluid 112 of the fluid system 104. In some embodiments, the fluid system 104 may be an oil system in which case the fluid 112 is oil. However, other embodiments may also apply. For instance, the magnetic chip detector 102 may be provided near a gearbox, near a pump or at any other suitable location in the fluid system 104. The two magnetic prongs 110 are spaced-apart by a gap 114 such that when one or more metallic chips ("the chip") bridge the gap 114, electricity can be conducted from one magnetic prong to the other, or vice versa. As it will be understood, any type of magnetic chip detector can be used. For instance, the magnetic chip detector 102 can have a single magnetic prong or more than two magnetic prongs. In one example, each magnetic prong may have a sixteenth of an inch in diameter, and the gap may be of three sixteenth of an inch. Other dimensions may also be used.

As shown, the resistance measurement circuit 106 is connected with the magnetic chip detector 102. In this way, the resistance measurement circuit 106 is configured to measure a resistance value R across the magnetic chip detector 102.

In some embodiments, the resistance measurement circuit 106 may be connected in parallel with the magnetic chip detector 102. For instance, in this embodiment, the resistance measurement circuit 106 includes an ohmmeter 116 connected to a circuit 118 including one or more electrical resistors 120 ("the resistor 120") connected in parallel with the two magnetic prongs 110 via conductors 122. The term "resistor" is meant to encompass any system, device, component or any combination thereof that can provide a suitable electrical resistance.

The parallel connection between the resistor 120 and the magnetic chip detector 102 can allow electricity to be conducted across the circuit 118 independently of whether or not the gap 114 is bridged by a chip.

As will be detailed herebelow, the resistance 120 allows for system fault detection. Indeed, in an embodiment wherein the resistor 120 is connected in parallel with the magnetic chip detector 102, a resistance limit value $R_{LIM}$ can be measured when the gap 114 is not bridged by chips. Accordingly, a circuit malfunction (e.g., a break in the conductor 122) can be determined when the resistance value R is above the resistance limit value $R_{LIM}$.

As depicted in this example, the resistor 120 is shown to be internal to the magnetic chip detector 102. However, in other embodiment, the resistor 120 may be external to the magnetic chip detector 102. For instance, the resistor 120 may be internal to the resistance measurement circuit 106. The resistor 120 may vary due to design. In some embodiments, providing the resistor 120 internally to the magnetic chip detector 102 can be desirable for reliability purposes. In some other embodiments, the resistor 120 is omitted.

In some embodiments, an excitation source 132 can be connected to the circuit 118 and in parallel with the two magnetic prongs 110 via conductors 122. The excitation source aims at providing sufficient current levels to overcome the "Branly's Effect", where small magnetic chips cease to be conductive at low currents. Other excitation sources or signal conditioning circuits, if applicable, may also be used. In this example, the excitation source 132 is independent of the engine computer 108, but in alternative embodiments, the excitation source 132 can be controlled by the engine computer 108.

An example of the ohmmeter 116 includes an electrical power source to apply a voltage V to the circuit 118 via a galvanometer to measure the current I through the circuit 118. Another example of the ohmmeter 116 includes a first circuit that passes a constant current I through the circuit 118, and a second circuit that measures the voltage V across the resistance. In both these examples, the resistance value R is given by the equation R=V/I according to Ohm's Law. Other suitable types of ohmmeters can be used.

In this example, the resistance measurement circuit 106 is part of the engine computer 108 such that the resistance measurement circuit 106 is housed within a housing 124 of the engine computer 108. In alternate embodiments, however, the resistance measurement circuit 106 and the engine computer 108 are provided in two separate housings operatively connected to one another.

As illustrated, the engine computer 108 is operatively connected to the resistance measurement circuit 106 to further process the measured resistance value R.

Figure 2:
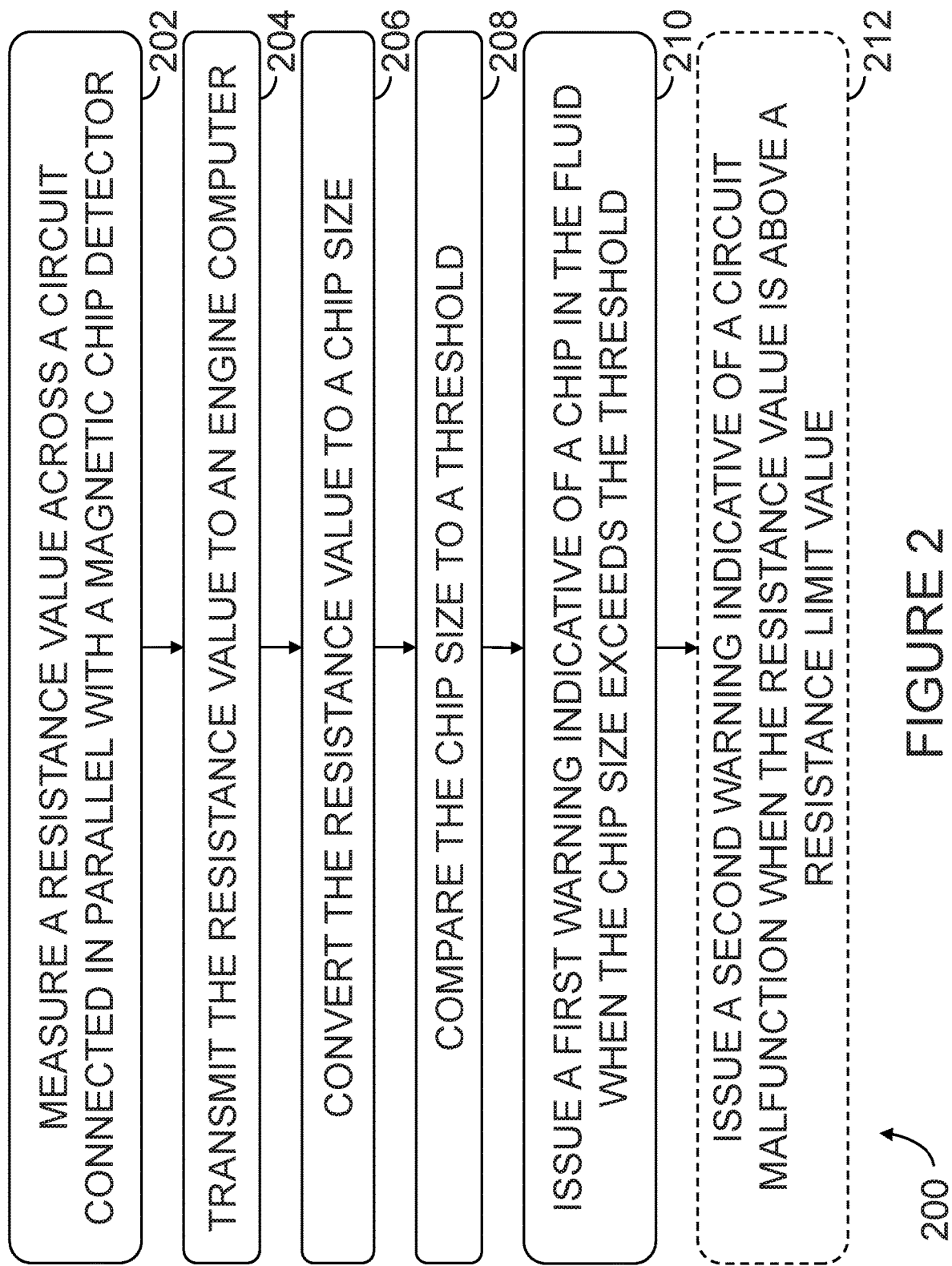
FIG. 2 is a flow chart of a first example method for detecting chips in fluid of the aircraft engine of FIG. 1.

FIG. 2 shows a flow chart of an exemplary method 200 for detecting chips in fluid of the aircraft engine. As it will be understood, the method 200 may be performed continuously or periodically as the aircraft engine is running. FIG. 2 will be described with reference to FIG. 1.

At step 202, a threshold is dynamically set in the engine computer 108 for detecting chips in the fluid 112.

The threshold may be dynamically set without modifying the hardware, which may be beneficial as the threshold can vary depending on the type of magnetic chip detector 102, on the location of the magnetic chip detector 102 in the fluid system 104 or on the type of aircraft engine. For instance, a given chip can be critical upstream from a gear box of the aircraft engine whereas the same given chip may not be critical at another location.

In some embodiments, the engine computer 108 may be configured to dynamically set the threshold based on a current condition of the aircraft engine and/or flight mission. For instance, the threshold can be dynamically modified based on the time of operation of the engine or aircraft. For instance, the engine computer 108 may have software to dynamically set the threshold to increase its sensitivity as the time of operation of the engine or aircraft increases. The software may also be used to decrease the sensitivity of the threshold.

In other embodiments, the engine computer 108 may dynamically set the threshold as function of a configuration of the aircraft engine. For instance, a common engine computer may be connected to different aircraft engines, and then the engine computer may have software apply different thresholds based on the aircraft engine configuration.

Indeed, the engine computer 108, when connected to a plurality of magnetic chip detectors located in a plurality of aircraft engines, may detect chips in fluid of each of the plurality of aircraft engines. In these embodiments, the engine computer 108 may dynamically set the threshold for each of the magnetic chip detectors without modifying hardware based on the aircraft engine on which each magnetic chip detector is installed, the excitation source 132 used, and/or the type of magnetic chip detector 102 connected to it. For instance, the engine computer 108 can be used to detect chips in fluid of different aircraft engines of a production line or, in alternate embodiments, the engine computer 108 can be used to detect chips in fluid of different aircraft engines in different production lines.

At steps 204 and 206, the resistance measurement circuit 106 measures the resistance value R across the circuit 118 and transmits the resistance value R to the engine computer 108.

At step 208, the engine computer 108 compares the resistance value to the threshold to determine whether the resistance value is below, equal or above the threshold.

In some embodiments, the engine computer 108 is connected to the resistance measurement circuit 106 in a manner that allows the engine computer 108 to read the resistance value R directly from the resistance measurement circuit 106.

At step 210, the engine computer 108 issues a first warning indicative of a chip in the fluid 112 when the resistance value exceeds the threshold.

For instance, the threshold can be 1000 ohms. Accordingly, in this specific embodiment, the engine computer 108 issues a first warning indicative of a chip in the fluid 122 when the resistance value R is above 1000 ohms. This exemplary threshold is provided as an example only. Other engines or installations may have other thresholds.

In some embodiments, the resistance value is monitored over time. In these embodiments, a gradual decrease in the resistance value may indicate the gradual accumulation of small chips (e.g., from normal engine wear and tear) whereas a sudden drop in the resistance value may indicate the presence of a large chip (e.g., from a major engine failure). In this specific embodiment, the first warning is issued when the resistance value is such that the working of the aircraft engine may be altered.

In other embodiments, the first warning is issued directly in the aircraft to the pilot(s) and/or the flight crew. This may be the case, for instance, when the magnetic chip detector 102 is positioned at a key location in the fluid system 104. In such embodiments, the warning may be embodied by activating a light in the cockpit or elsewhere in the aircraft. The warning may also be audible, or some other form of visual warning, such as text or graphic on a display. Other embodiments may also apply.

In some other embodiments, the magnetic chip detector 102 allows the first warning to be issued to a computer-readable memory for storing thereof. In this case, the first warning may be accessed during maintenance of the aircraft engine.

At step 212, the engine computer 108 may issue a second warning indicative of a circuit malfunction when the resistance value R is above a resistance limit value $R_{LIM}$. In this step, measuring a resistance value R above the resistance limit value $R_{LIM}$ can indicate that the ohmmeter 116 measures the resistance of an open circuit. Such an open circuit can be caused by a broken wire in the resistance measurement circuit 106 or by a broken conductor 122, for instance.

In some embodiments, the resistance limit value $R_{LIM}$ is stored on a computer-readable memory which is accessible by the engine computer 108. For instance, the resistance limit value $R_{LIM}$ may have been previously stored on a computer-readable memory of the engine computer 108.

In alternate embodiments, at step 208, the engine computer 108 converts the resistance value to a chip size and then compares the chip size to the threshold so that the engine computer 108 issues a first warning when the chip size exceeds the threshold. For instance, in one specific embodiment, the threshold is 0.010 inch. Therefore, in this embodiment, the engine computer 108 issues a first warning indicative of a chip in the fluid 112 when the chip size exceeds 0.010 inch.

In these embodiments, the chip size refers to the size of a single chip bridging the gap 114 whereas, in other embodiments, the chip size refers to the size of a plurality of chips bridging the gap 114. The engine computer 108 may convert the resistance value R to the chip size using conversion data that is stored on a computer-readable memory which is accessible by the engine computer 108. In some embodiments, the conversion data may be provided in the form of a lookup table. For instance, in one specific embodiment, the lookup table can be indicative that the chip size is equal or above to 0.020 inch when the resistance value R is below or equal to 300 ohms, that the chip size is equal to 0.020 inch when the resistance value is 500 ohms, or that the chip size is below or equal to 0.004 inch when the resistance value R is equal or above to 20,000 ohms. These exemplary values can vary from one embodiment to another as the resistance value R may depend on the voltage applied across the gap 114 and on the circuitry of the engine computer 108, for instance. In alternate embodiments, the conversion data may be provided in the form of a mathematical relation. However, the conversion data may be provided in any other suitable form. For instance, the conversion data may have been previously stored on a computer-readable memory of the engine computer 108.

Figure 3:
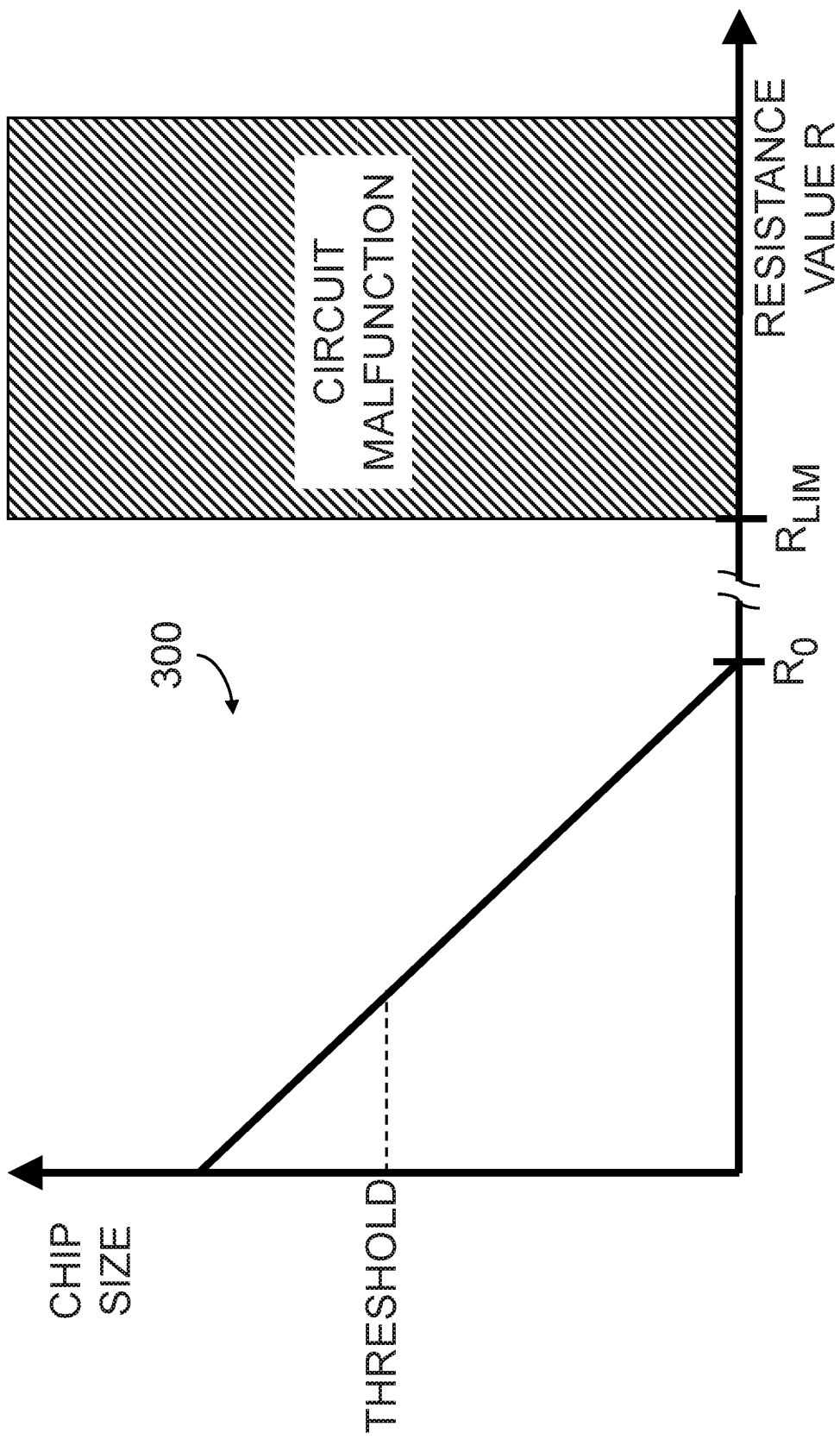
FIG. 3 is a graph showing an exemplary relation between chip size and resistance value.

FIG. 3 is a graph 300 showing an exemplary relation between chip size and resistance value.

As shown, the chip size varies inversely proportionally to the resistance value R. Accordingly, the bigger the measured resistance value R, the lesser the chip size of the chip bridging the gap 144 of the magnetic chip detector 102. The linear relationship showed in FIG. 3 is exemplary only. The relationship between the chip size and the resistance value R can vary.

When the gap 114 is not bridged by any chip (i.e. chip size equals zero), electricity is not expected to be conducted across the two magnetic prongs 110 of the magnetic chip detector 102. In this situation, the resistance value R of the circuit 118 is thus given by the given resistance value $R_0$ of the resistor 120.

The engine computer 108 can convert the resistance value R to a chip size when the resistance value R is comprised between 0 and the given resistance value $R_0$. When the resistance value R is above the resistance limit value $R_{LIM}$, the second warning may be issued, as per step 212. In some embodiments, the given resistance $R_0$ corresponds to the resistance limit value $R_{LIM}$.

Alternatively, or in combination therewith, the method 200 may include a step of displaying the chip size on an aircraft instrument, such as on a gauge 126 of a cockpit 128, as shown in FIG. 1. In some embodiments, the gauge 126 or other visual indicator of chip size may include the threshold and the visual indicator is updated dynamically to display the current chip size as being above or below the threshold. For example, the threshold may be defined by a zone 130 on the gauge 126. Alternatively, the visual indicator is modified, such as in color, size, or shape, when the chip size exceeds the threshold. Other embodiments for displaying chip size along a scale and updating in real-time may also be used.

In some embodiments, the display of the chip size may be separated in three categories: small, medium, and critical based on two or more thresholds. A first threshold may differentiate medium chip size from critical chip size, and a second threshold, smaller than the first threshold, may differentiate small chip size from medium chip size. In this embodiment, the displaying may include activating a green LED when the chip size is small (i.e. chip size is below the second threshold), the displaying may include activating a yellow LED when the chip size is medium (i.e. chip size is between the second threshold and the first threshold) and displaying may include activating a red LED when the chip size is critical (i.e. chip size exceeds the first threshold). The display of chip size may be separated into more or less than three categories, depending on the circumstances.

In some embodiments, the measured resistance value R is continuously stored in the engine computer 108 or transmitted to an external server/computer for engine health monitoring, treading and analysis. Storing the resistance value R can allow monitoring of the resistance value R over time.

Figure 4:
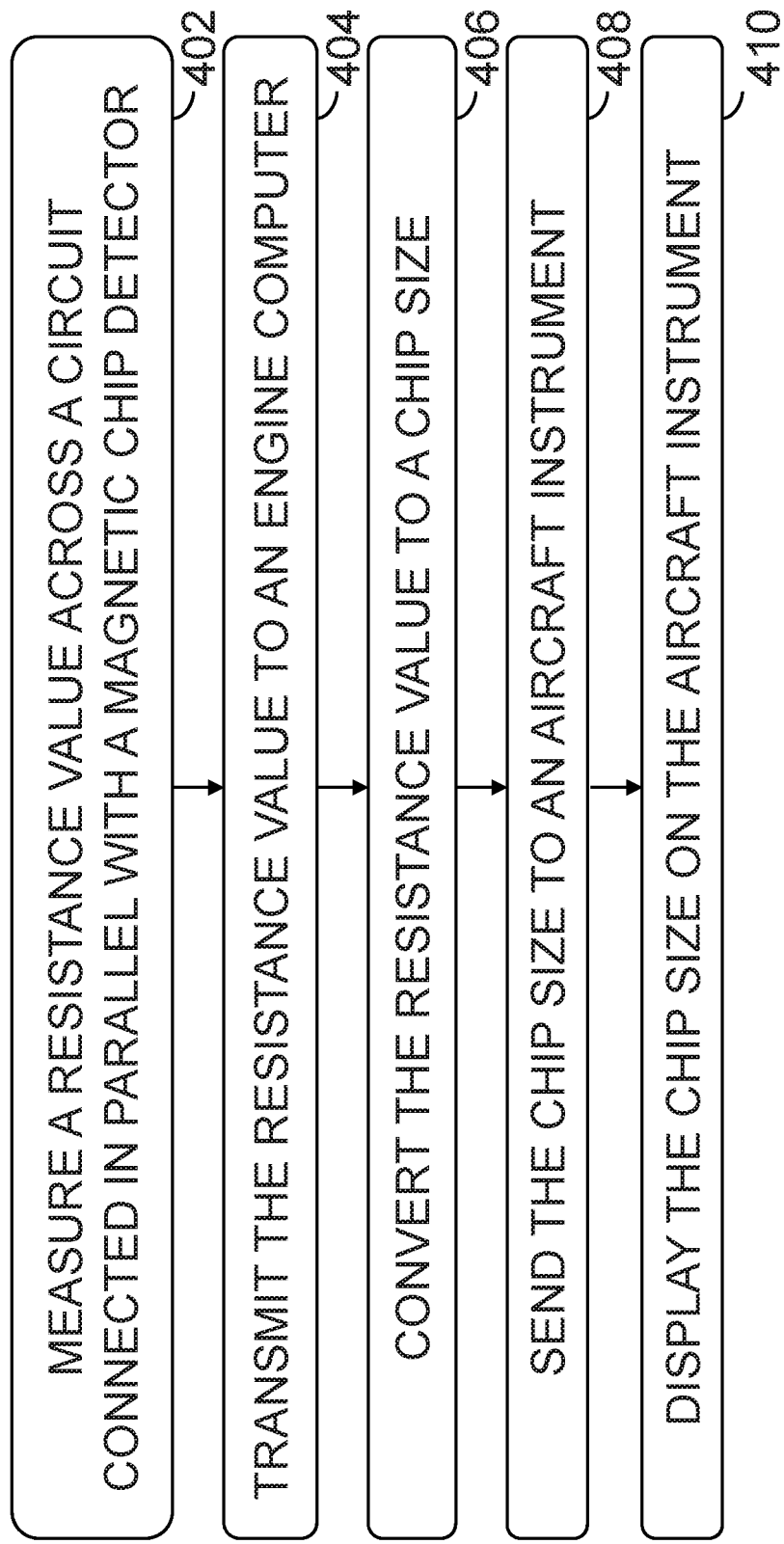
FIG. 4 is a flow chart of a second example method for detecting chips in fluid of the aircraft engine of FIG. 1.

FIG. 4 shows a flow chart of an exemplary method 400 for detecting chips in fluid of the aircraft engine. As it will be understood, the method 400 may be performed continuously or periodically as the aircraft engine is running. FIG. 4 will be described with reference to FIG. 1.

As depicted, the method 400 includes steps 402 and 404 which are similar to steps 204 and 206 of the method 200, respectively. Steps 402 and 404 will thus not be described in detail and the embodiments described above with reference to the steps 204 and 206 also apply to the steps 402 and 404 of the method 400.

At step 406, similarly to an embodiment of step 208 described above, the engine computer 108 converts the resistance measurement to a chip size.

At step 408, the engine computer 108 sends the chip size to an aircraft instrument, such as the gauge 126 of the cockpit 128 shown in FIG. 1. Although shown in the cockpit 128 of the aircraft, the aircraft instrument may be located anywhere in the aircraft. In some embodiments, the chip size is sent via a wired connection between the engine computer 108 and the aircraft instrument. A wireless connection between the engine computer 108 and the aircraft display 126 may also be used.

At step 410, the chip size is displayed on the aircraft instrument. In some embodiments, the numerical value of the chip size is displayed using a gauge or an LCD display. Any other suitable type of display may be used. Accordingly, the step of dynamically setting the threshold in the engine computer 108 can be omitted. As described above, in some other embodiments, the threshold is based on the resistance value R. Accordingly, in these embodiments, the step of comparing the resistance value to the threshold may not include a step of converting the resistance value to a chip size and a step of comparing the chip size to the threshold may be omitted.

Figure 5:
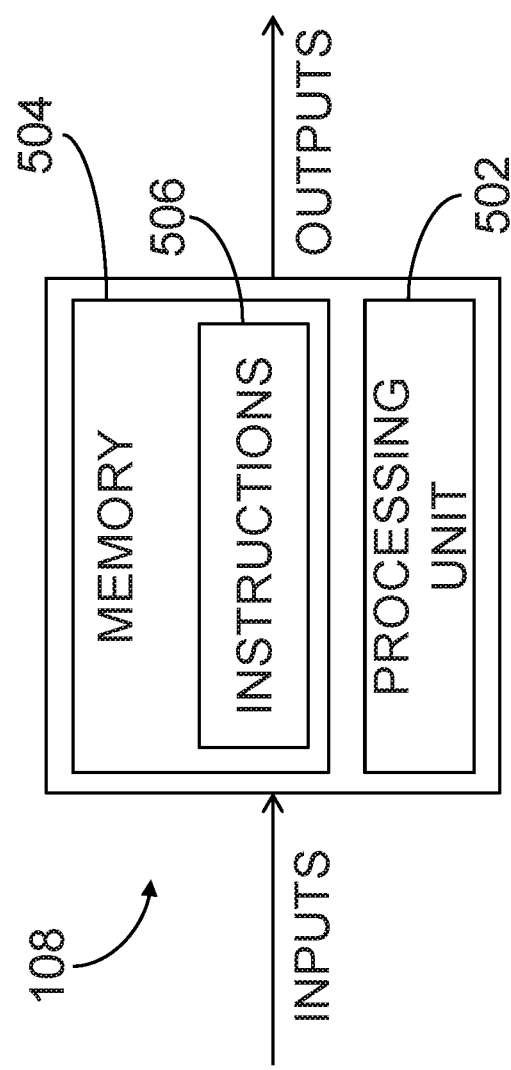
FIG. 5 is a block diagram of an example computing device for implementing the method of FIG. 2.

FIG. 5 shows a schematic representation of the engine computer 108, as a combination of software and hardware components. In this example, the engine computer 108 is illustrated with one or more processing units (referred to as "the processing unit 502") and one or more computer-readable memories (referred to as "the memory 504") having stored thereon program instructions 506 configured to cause the processing unit 502 to generate one or more outputs based on one or more inputs. The inputs may comprise one or more signals representative of the measured resistance value R, the threshold(s), the excitation levels associated with the excitation source, and the like. The outputs may comprise one or more signals representative of the first warning, the second warning, the chip size and the like.

The processing unit 502 may comprise any suitable devices configured to cause a series of steps to be performed so as to implement the computer-implemented methods 200, 400 such that the instructions 506, when executed by the engine computer 108 or other programmable apparatuses, may cause the functions/acts/steps specified in the methods described herein to be executed. The processing unit 502 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 504 may comprise any suitable known or other machine-readable storage medium. The memory 504 may comprise non-transitory computer readable storage medium such as, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions executable by the processing unit 502.

Each computer program described herein may be implemented in a high level procedural or object oriented programming or scripting language, or a combination thereof, to communicate with an engine computer. Alternatively, the programs may be implemented in assembly or machine language. The language may be a compiled or an interpreted language. Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

Figure 6:
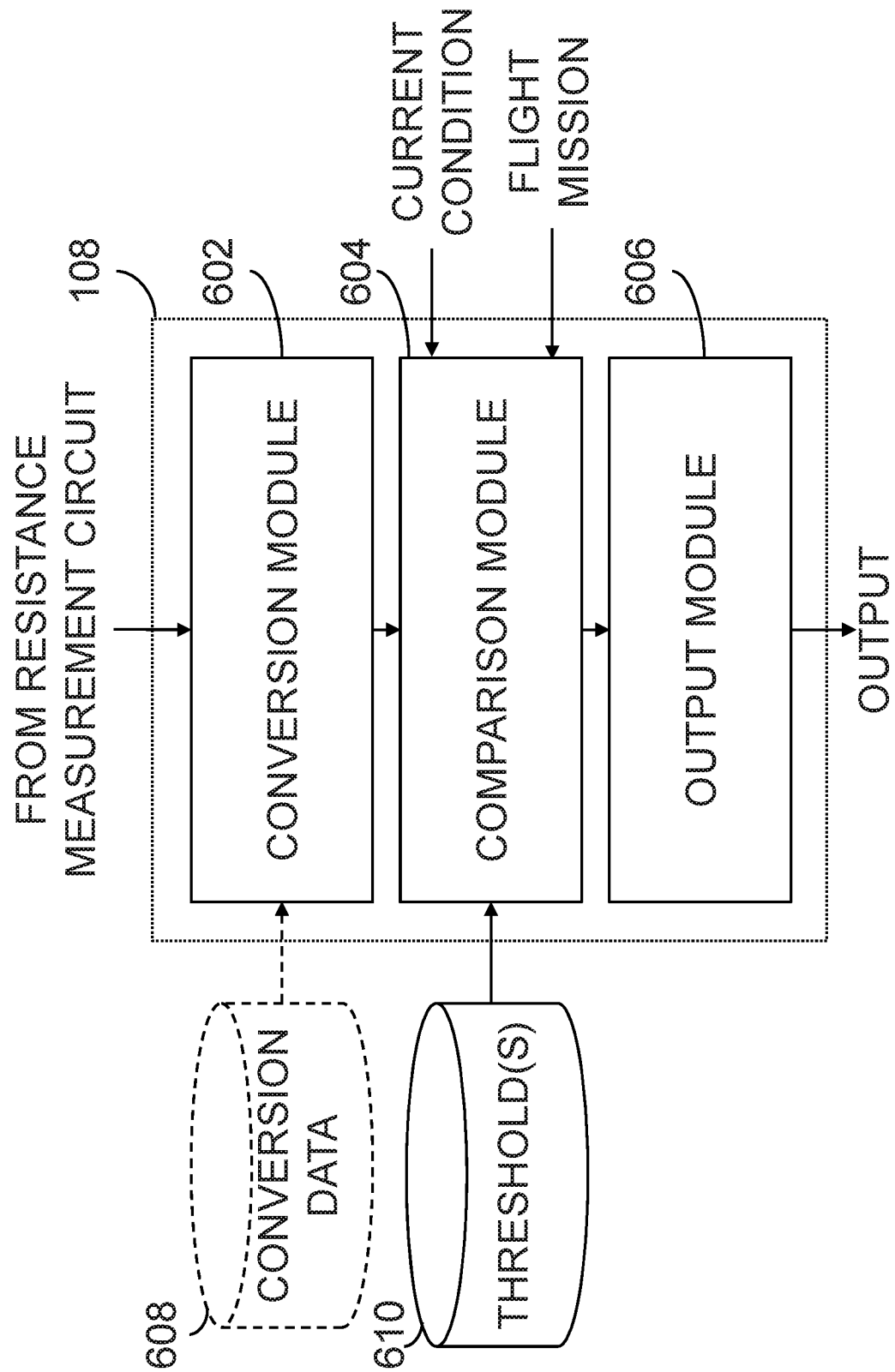
FIG. 6 is a block diagram of an example embodiment of the computing device of FIG. 5.

FIG. 6 shows a block diagram of an exemplary embodiment of the engine computer 108. As depicted, a conversion module 602, a comparison module 604 and an output module 606 embody the instructions 506 shown in FIG. 5.

The conversion module 602 is configured to receive the resistance value R from the resistance measurement circuit 106, to access the conversion data if necessary, and to convert the resistance value R to a chip size, as per a specific embodiment of step 206. The conversion module 602 may be coupled to a first database 608 storing the conversion data. Once the conversion is made, the chip size is provided to the comparison module 604.

The comparison module 604 is configured to receive the chip size from the conversion module 602, and to compare the chip size to the threshold, as per step 208. In alternate embodiments, the conversion module 102 is omitted and the comparison module 604 is configured to receive the resistance value from the resistance measurement circuit 106 and to compare the resistance value to the threshold. Once the comparison is made, the result of the comparison is provided to the output module 606.

In some embodiments, the comparison module 604 may be coupled to a second database 610 storing one or more thresholds. and which is accessible by the comparison module 604. For instance, the threshold may have been previously stored on the second database 601 and be set to a constant value for the lifetime of the engine.

The comparison module 604 may be configured to receive current conditions of the aircraft engine and to dynamically set the threshold based on the current condition. Alternatively, the threshold may be modified manually by accessing the engine computer 108 and setting the threshold as desired.

The comparison module 604 may also be configured to dynamically set the threshold as function of a flight mission.

The output module 606 is configured to receive the result of the comparison from the comparison module 604, and to output a first warning indicative of a chip in the fluid when the chip size exceeds the threshold, as per step 210. Previously issued warnings can form history data representative of the evolution of the chip size of the chip across the gap of the magnetic chip detector over time. In other words, the output of the resistance measurement circuit 106 may be monitored continuously by the engine computer 108.

The databases 608, 610 may be provided locally to the engine computer 108, or remotely therefrom (e.g., from a database of an aircraft computer or remotely from the aircraft). In some embodiments, the first and second databases 608, 610 are provided in the form of a single database accessible by the conversion module 602, the comparison module 604 and the output module 606. In addition, although shown as separate from the engine computer 108, the databases 608, 610 may be integrated therewith. For instance, the databases 608, 610 may correspond to the memory 504 of the engine computer 108.

The output module 606 can also be configured to issue a second warning indicative of a circuit malfunction when the resistance value is above the resistance limit value $R_{LIM}$, as per step 212. The resistance limit value $R_{LIM}$ may be stored on the first database 608, on the second database 610 or on any other database accessible by the engine computer 108.

Figure 7:
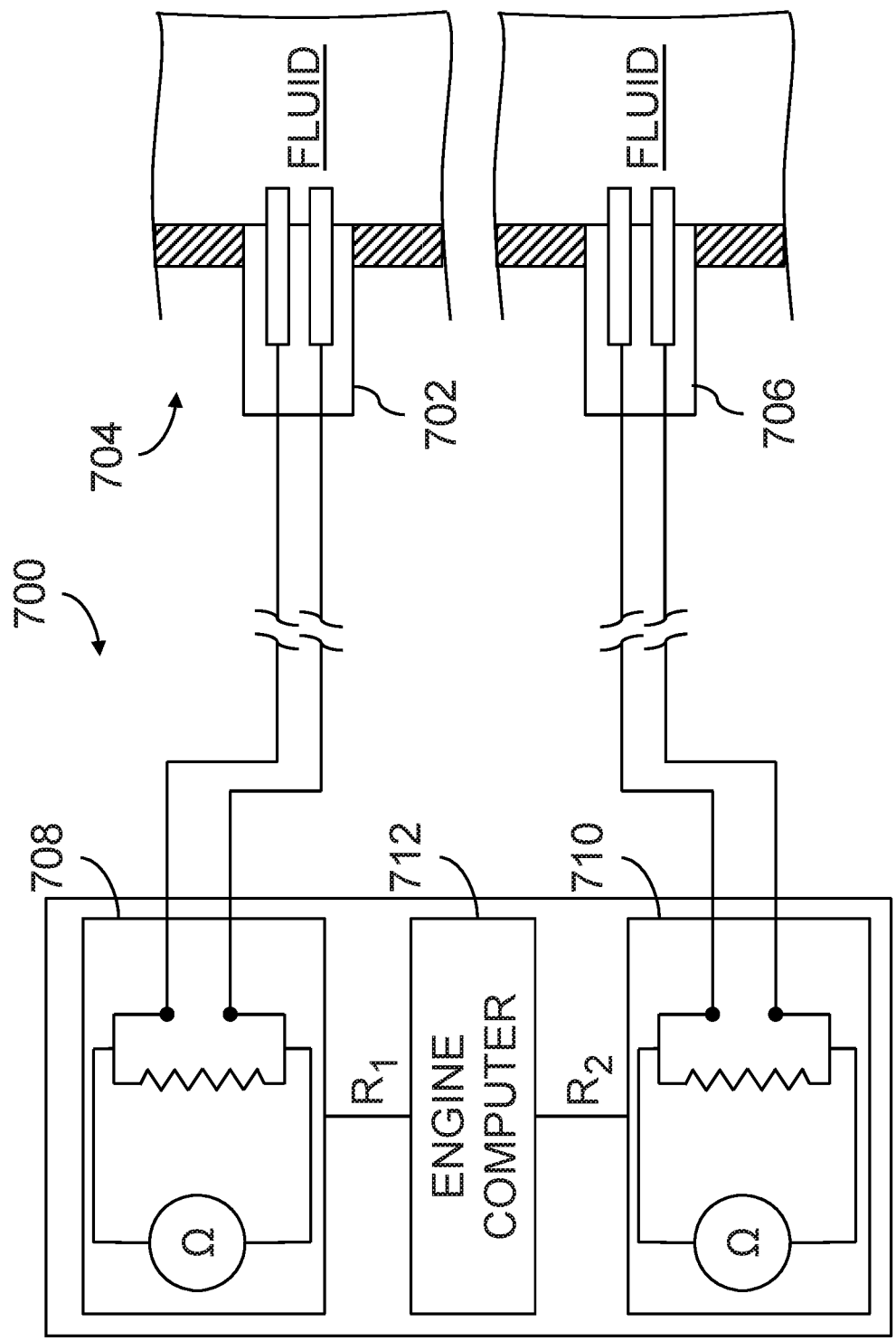
FIG. 7 is a schematic view of another example of a chip detection system incorporating first and second magnetic chip detectors.

In some embodiments, a plurality of magnetic chip detectors are mounted to a same engine and are operated as a network of magnetic chip detectors. FIG. 7 is a schematic view of an example embodiment. As depicted in this example, a detection system 700 has a first magnetic chip detector 702 mounted at a first location of a fluid system 704 and a second magnetic chip detector 706 mounted at a second location of the fluid system 704. Each of the first and second magnetic chip detectors 702, 706 may be similar to the magnetic chip detector 102 described above with reference to FIG. 1.

The detection system 700 includes a first resistance measurement circuit 708 and a second resistance measurement circuit 710 both connected to a respective one of the first and second magnetic chip detectors 702, 706 and to the engine computer 712. Each of the first and second resistance measurement circuits 708, 710 may be similar to the resistance measurement circuit 106 described with reference to FIG. 1.

As it will be understood, the first resistance measurement circuit 708 is configured to measure a first resistance value $R_1$ from the first magnetic chip detector 702, and the second resistance measurement circuit 710 is configured to measure a second resistance value $R_2$ from the second magnetic chip detector 706. Both the first and second resistance measurement circuits 708, 710 are configured to transmit the first and second resistance values $R_1$, $R_2$ to the engine computer 712.

In this embodiment, the engine computer 712 receives the resistance values $R_1$, $R_2$ measured by the first and second resistance measurement circuits 708, 710. The method 200 described with reference to FIG. 2 or the method 400 described with reference to FIG. 4 can thus be performed with both the first and second magnetic chip detectors 702, 706 concurrently or consecutively.

In some embodiments, the first and second resistance values $R_1$, $R_2$ are compared to a threshold. In some other embodiments, the first and second resistance values $R_1$, $R_2$ are converted to first and second chip sizes which are then compared to a threshold.

In some other embodiments, the first chip size is compared to a first threshold, and the second chip size is compared to a second threshold different from the first threshold. For instance, the first threshold can be based on the first location of the first magnetic chip detector and the second threshold can be based on the second location of the second magnetic chip detector.

It is noted that the first threshold and the second threshold can be independently tunable. For instance, depending on a current condition of the aircraft engine or on a flight mission, the first threshold may be kept constant while the second threshold is tuned, or vice versa.

Although the embodiment of FIG. 7 shows that each of the magnetic chip detector 702, 706 has its dedicated resistance measurement circuit 708, 710, in some embodiments, a single resistance measurement circuit may be used. In such a case, the single resistance measurement circuit may be connected to each of the magnetic chip detectors via electrical switches. The engine computer 712 may thus monitor the resistance value of each of the magnetic chip detectors 702, 706 by actuating the electrical switches accordingly. Such monitoring may be performed in a pre-determined manner, or in a random or pseudo-random manner, and the monitoring may be performed more frequently for magnetic chip detectors located at key locations of the fluid system than for magnetic chip detectors at non-key locations of the fluid system.

The above description is meant to be exemplary only, and one skilled in the art will recognize that changes may be made to the embodiments described without departing from the scope of the invention disclosed. For example, the methods and systems described therein are applicable to any type of commercial or military aircraft engines having an engine computer. Still other modifications which fall within the scope of the present invention will be apparent to those skilled in the art, in light of a review of this disclosure, and such modifications are intended to fall within the appended claims.

The invention claimed is:

1. A method for detecting chips in fluid of an aircraft engine, the method comprising:
dynamically setting, in an engine computer, a first threshold for detecting chips in the fluid, wherein the first threshold is set as a function of a configuration of the aircraft engine;
measuring a resistance value across a first magnetic chip detector mounted to a fluid system of the aircraft engine at a first location and transmitting the resistance value to the engine computer of the aircraft engine;
comparing, in the engine computer, the resistance value to the first threshold; and issuing, from the engine computer, a first warning indicative of a chip in the fluid when the resistance value exceeds the first threshold.

2. The method of claim 1, wherein comparing the resistance value to the first threshold comprises converting the resistance value to a chip size based on a correlation between resistance and chip size, and comparing the chip size to the first threshold.

3. The method of claim 2, further comprising displaying the chip size on a display of the aircraft.

4. The method of claim 1, wherein measuring a resistance value comprises measuring the resistance value across a circuit connected in parallel with the first magnetic chip detector.

5. The method of claim 4, further comprising issuing, from the engine computer, a second warning indicative of a circuit malfunction when the resistance value is above a resistance limit value.

6. The method of claim 1, wherein the method is performed continuously as the aircraft engine is running.

7. The method of claim 1, wherein measuring the resistance value comprises measuring the resistance value over time.

8. A method for detecting chips in fluid of an aircraft engine, the method comprising:
dynamically setting, in an engine computer, a first threshold for detecting chips in the fluid;
measuring a resistance value across a first magnetic chip detector mounted to a fluid system of the aircraft engine at a first location and transmitting the resistance value to the engine computer of the aircraft engine;
comparing, in the engine computer, the resistance value to the first threshold;
issuing, from the engine computer, a first warning indicative of a chip in the fluid when the resistance value exceeds the first threshold;
dynamically setting a second threshold independently tunable from the first threshold;
measuring a resistance value across a second magnetic chip detector mounted to the fluid system of the engine at a second location;
comparing the resistance value from the second magnetic chip detector to the second threshold; and
issuing a second warning indicative of a chip in the fluid when the resistance value from the second magnetic chip detector exceeds the second threshold.

9. A chip detection system for an aircraft engine, the detection system comprising:
a magnetic chip detector mounted to a fluid system of the aircraft engine at a first location;
a resistance measurement circuit comprising a circuit connected in parallel with the magnetic chip detector and configured for measuring a resistance value across the magnetic chip detector; and
an engine computer coupled to the resistance measurement circuit and configured for:
dynamically setting a first threshold for detecting chips in the fluid;
receiving the resistance value from the resistance measurement circuit;
comparing the resistance value to the first threshold;
issuing a first warning indicative of a chip in the fluid when the resistance value exceeds the first threshold; and
issuing a second warning indicative of a circuit malfunction when the resistance value is above a resistance limit value.

10. The detection system of claim 9, wherein comparing the resistance value to the first threshold comprises converting the resistance value to a chip size based on a correlation between resistance and chip size, and comparing the chip size to the first threshold.

11. The detection system of claim 10, wherein the engine computer is further configured for transmitting a signal for displaying the chip size on a display of the aircraft.

12. The detection system of claim 9, wherein dynamically setting a first threshold comprises setting the first threshold based on at least one of a current condition of the aircraft engine and a flight mission.

13. The detection system of claim 9, wherein dynamically setting the first threshold comprises setting the first threshold as function of a configuration of the aircraft engine.

14. The detection system of claim 9, wherein measuring the resistance value comprises measuring the resistance value over time.

15. The detection system of claim 9, further comprising a second magnetic chip detector mounted to the fluid system of the engine at a second location, and having a second threshold independently tunable from the first threshold.

16. A method for detecting chips in fluid of an aircraft engine, the method comprising:
dynamically setting, in an engine computer, a first threshold for detecting chips in the fluid;
measuring a resistance value across a circuit connected in parallel with a first magnetic chip detector mounted to a fluid system of the aircraft engine and transmitting the resistance value to the engine computer of the aircraft engine;
comparing, in the engine computer, the resistance value to the first threshold;
issuing, from the engine computer, a first warning indicative of a chip in the fluid when the resistance value exceeds the first threshold; and
issuing, from the engine computer, a second warning indicative of a circuit malfunction when the resistance value is above a resistance limit value.

17. The method of claim 16, wherein comparing the resistance value to the first threshold comprises converting the resistance value to a chip size based on a correlation between resistance and chip size, and comparing the chip size to the first threshold.

18. The method of claim 17, further comprising transmitting a signal for displaying the chip size on a display of the aircraft.

19. The method of claim 16, wherein measuring the resistance value comprises measuring the resistance value over time.

* * * * *